(12) United States Patent
Alexander et al.

(10) Patent No.: US 10,028,739 B2
(45) Date of Patent: Jul. 24, 2018

(54) SYSTEMS, TOOLS, AND METHODS FOR CONNECTING TO TISSUE

(71) Applicant: Boston Scientific Scimed, Inc., Maple Grove, MN (US)

(72) Inventors: James A. Alexander, Excelsior, MN (US); Thomas O. Viker, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 265 days.

(21) Appl. No.: 14/775,188

(22) PCT Filed: Mar. 11, 2014

(86) PCT No.: PCT/US2014/023337
§ 371 (c)(1),
(2) Date: Sep. 11, 2015

(87) PCT Pub. No.: WO2014/150468
PCT Pub. Date: Sep. 25, 2014

(65) Prior Publication Data
US 2016/0015382 A1   Jan. 21, 2016

Related U.S. Application Data

(60) Provisional application No. 61/789,179, filed on Mar. 15, 2013.

(51) Int. Cl.
*A61B 17/064*    (2006.01)
*A61B 17/42*    (2006.01)
(Continued)

(52) U.S. Cl.
CPC .......... *A61B 17/064* (2013.01); *A61B 17/068* (2013.01); *A61B 17/0643* (2013.01);
(Continued)

(58) Field of Classification Search
CPC .............. A61B 17/064; A61B 17/0643; A61B 17/0644; A61B 2017/0641; A61B 2017/0419; A61F 2/00–2/0063
See application file for complete search history.

(56) References Cited

U.S. PATENT DOCUMENTS

| 4,873,976 A | 10/1989 | Schreiber |
| 5,112,344 A | 5/1992 | Petros |

(Continued)

FOREIGN PATENT DOCUMENTS

| EP | 0 774 240 A1 | 5/1997 |
| WO | WO97/47244 | 12/1997 |

(Continued)

OTHER PUBLICATIONS

Extended European Search Report for European Application No. 14767697.7, dated Jan. 24, 2017, 5 pages.

*Primary Examiner* — Thaddeus Cox
(74) *Attorney, Agent, or Firm* — Brake Hughes Bellermann LLP

(57) ABSTRACT

Described are various embodiments of surgical procedure systems, devices, tools, and methods, useful for connecting tissue (e.g., soft tissue, organ tissue) to another tissue or to a surgical device such as an implant; specific methods can be useful for plastic surgery, treating pelvic conditions such as vaginal prolapse, incontinence, and other conditions caused by muscle and ligament weakness, and for general surgical procedures.

20 Claims, 7 Drawing Sheets

(51) Int. Cl.
*A61B 17/06* (2006.01)
*A61B 17/068* (2006.01)
A61B 17/00 (2006.01)
A61B 17/04 (2006.01)

(52) U.S. Cl.
CPC .. *A61B 17/06066* (2013.01); *A61B 17/06109* (2013.01); *A61B 17/42* (2013.01); *A61B 2017/00792* (2013.01); *A61B 2017/00805* (2013.01); *A61B 2017/0419* (2013.01); *A61B 2017/0608* (2013.01); *A61B 2017/0645* (2013.01)

(56) References Cited

U.S. PATENT DOCUMENTS

| | | | |
|---|---|---|---|
| 5,209,756 | A | 5/1993 | Seedhom et al. |
| 5,611,515 | A | 3/1997 | Benderev et al. |
| 5,842,478 | A | 12/1998 | Benderev et al. |
| 5,860,425 | A | 1/1999 | Benderev et al. |
| 5,899,909 | A | 5/1999 | Claren et al. |
| 5,972,000 | A | 10/1999 | Beyar et al. |
| 6,039,686 | A | 3/2000 | Kovac |
| 6,042,534 | A | 3/2000 | Gellman et al. |
| 6,071,290 | A | 6/2000 | Compton |
| 6,099,552 | A | 8/2000 | Adams |
| 6,110,101 | A | 8/2000 | Tihon et al. |
| 6,612,977 | B2 | 9/2003 | Staskin et al. |
| 6,648,921 | B2 | 11/2003 | Anderson et al. |
| 6,691,711 | B2 | 2/2004 | Raz et al. |
| 7,025,063 | B2 | 4/2006 | Snitkin et al. |
| 7,303,525 | B2 | 12/2007 | Watschke et al. |
| 7,347,812 | B2 | 3/2008 | Mellier |
| 7,351,197 | B2 | 4/2008 | Montpetit et al. |
| 7,407,480 | B2 | 8/2008 | Staskin et al. |
| 7,500,945 | B2 | 3/2009 | Cox et al. |
| 2002/0147382 | A1 | 10/2002 | Neisz et al. |
| 2002/0151762 | A1 | 10/2002 | Rocheleau et al. |
| 2004/0010245 | A1* | 1/2004 | Cerier ............... A61B 17/00234 606/1 |
| 2005/0187565 | A1 | 8/2005 | Baker et al. |
| 2005/0261710 | A1 | 11/2005 | Sakamoto et al. |
| 2005/0273124 | A1 | 12/2005 | Chanduszko |
| 2008/0300624 | A1* | 12/2008 | Schwemberger .... A61B 17/064 606/213 |
| 2009/0093824 | A1* | 4/2009 | Hasan ................ A61B 17/0401 606/139 |
| 2010/0094341 | A1 | 4/2010 | Raju |
| 2010/0174134 | A1 | 7/2010 | Anderson et al. |
| 2010/0256442 | A1 | 10/2010 | Ogdahl et al. |
| 2010/0292793 | A1 | 11/2010 | Höglund |
| 2010/0298630 | A1 | 11/2010 | Wignall |
| 2011/0034759 | A1 | 2/2011 | Ogdahl et al. |
| 2011/0071548 | A1* | 3/2011 | Yeh .................... A61B 17/0057 606/144 |
| 2011/0224698 | A1 | 9/2011 | Deitch et al. |
| 2012/0022318 | A1 | 1/2012 | Thierfelder et al. |
| 2012/0145765 | A1* | 6/2012 | Peterson ............. A61B 17/064 227/175.1 |
| 2013/0006061 | A1 | 1/2013 | Alexander et al. |
| 2013/0035543 | A1 | 2/2013 | Fischer et al. |
| 2013/0035555 | A1 | 2/2013 | Alexander et al. |
| 2014/0031835 | A1* | 1/2014 | Viker ................ A61B 17/12009 606/119 |
| 2014/0236193 | A1* | 8/2014 | Chin .................. A61B 17/0469 606/145 |
| 2014/0257339 | A1* | 9/2014 | Levy .................... A61B 17/068 606/139 |

FOREIGN PATENT DOCUMENTS

| | | |
|---|---|---|
| WO | 2002/38079 A | 5/2002 |
| WO | 2003/068107 A1 | 8/2003 |
| WO | 2003/073960 A1 | 9/2003 |
| WO | 2003/096929 A1 | 11/2003 |
| WO | WO2007/097994 | 8/2007 |
| WO | WO2007/149348 | 12/2007 |
| WO | WO2008/057261 | 5/2008 |
| WO | WO2010/093421 | 8/2010 |
| WO | WO2011/063412 | 5/2011 |
| WO | WO2011/072148 | 6/2011 |
| WO | WO2011/082350 | 7/2011 |
| WO | WO2011091275 | 7/2011 |
| WO | 2012088232 A2 | 6/2012 |
| WO | WO2012/177305 | 12/2012 |
| WO | 2013179106 A1 | 12/2013 |

\* cited by examiner

SYSTEMS, TOOLS, AND METHODS FOR CONNECTING TO TISSUE

CROSS-REFERENCE TO RELATED APPLICATIONS

This application claims the benefit from International Application No. PCT/US2014/023337, filed Mar. 11, 2014, which in turn claims priority under 35 USC 119(e) from U.S. Provisional Patent Application No. 61/789,179, filed Mar. 15, 2013 and titled "SYSTEMS, TOOLS, AND METHODS FOR CONNECTING TO TISSUE", the disclosures of which are incorporated herein by reference in their entireties.

FIELD OF THE INVENTION

The invention relates generally to systems, tools, and related methods for connecting anatomical tissue (e.g., soft tissue or an organ) to tissue or for connecting tissue to another item such as a surgical implant. Exemplary methods include surgically treating a condition by making a connection to tissue, e.g., by connecting tissue or an implant to tissue, for example to treat a pelvic condition, during plastic surgery, or for other types of specific or general surgical procedures. In methods specific to treating a pelvic condition, the pelvic condition may be any condition treated by placement of an implant in a male or female patient, including but not limited to a condition of levator tissue; incontinence (urinary or fecal); hernia repair, and prolapse conditions, for example treatment of vaginal and vaginal vault prolapse; a method can be performed by an open surgical procedure, by a transvaginal, abdominal, or laparoscopic procedure, or by other surgical methods.

BACKGROUND

The fields of medicine and surgical medicine involve methods and structures useful for connecting tissue, and for connecting surgical items such as implants to tissue. Medical and surgical sutures are ubiquitous. These can take the form of a natural or synthetic thread or other fibrous or filamentary structure that is passed through tissue, optionally passed through or around an implant or other surgical item, and then tied off to secure the tissue or tissue and surgical item in place.

The use of sutures is not perfect or even highly suitable for all surgical and medical procedures. For example, sutures are best tied by a surgeon or other medical professional manually, with assistance of tools such as a suture passing needle, forceps, and other surgical tools. This works well when the surgeon or medical professional has open access to the site of the suture, but less well when the suture must be tied in a constrained location or through tight access to the location. For those situations, a surgeon may experience difficulty placing the suture at its most effective or desired location, and tying the suture to best secure tissue to tissue or tissue to an implant.

Potential replacements for sutures have long been the subject of product research. Over time, countless examples of non-suture suture-replacement devices, related delivery tools, and related methods, have been developed and tried in efforts to replace the ubiquitous suture with an easier to use device. Examples include surgical staples and biologic adhesives useful to hold tissue to tissue or tissue to implants, and soft tissue anchors useful to secure surgical implants directly at patient tissue. Many of these have been used in particular applications that require placement of a suture at a difficult-to-reach surgical site or through a tight or deep surgical access path. Examples of these types of applications include surgical procedures that are performed laparoscopically, and surgical procedures that are performed transvaginally in a female patient or through a comparable medial or perineal tissue surgical access incision in a male patient. Many of these procedures are performed for treating a pelvic health condition such as prolapse or incontinence.

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), conditions of the pelvic floor such as levator tissue, and hernias.

Incontinence includes all various forms of anal (fecal) and urinary incontinence in a male or female. Vaginal prolapse in a female patient can be in the form of a cystocele, rectocele, enterocele, or vaginal vault prolapse, some of which can occur in combination with anal or urinary incontinence. In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times. Sacralcolpopexy (SCP) procedures are considered to be especially efficacious methods for treating vaginal vault prolapse. Various methods of placing slings or other implants for treating urinary or fecal continence are commonly used.

Still, there ongoing research and development of new and effective methods of surgically connecting tissue or surgically placing supportive implants for treating pelvic conditions in male and female patients, such as hernias, vaginal prolapse, incontinence, and other conditions affecting pelvic tissue and function. More generally, continuing interest exists for suture replacements in general surgical procedures in both humans and animals (i.e., in veterinary medicine), and in specific surgical specialties (e.g., plastic surgery).

SUMMARY

The following relates to medical or surgical devices, systems, methods that are useful to connect a surgical item to tissue, or to connect another tissue to tissue, and that do not involve a conventional medical suture or a medical staple (e.g., "sutureless connectors" for connecting two items). The items may both be anatomical or one item may be anatomical and another item may be an item placed during a surgical procedure such as a surgical implant. An anatomical item can be tissue or an organ (an "organ" being a specific type of "tissue"); a tissue or organ may be any anatomical tissue such as muscle, tendon, ligament, fascia, lumenal tissue such as a urethra, vaginal tissue, tissue of a bladder or bladder neck, cardiac tissue, skin (e.g., dermis, epidermis, etc.), subcutaneous tissue, etc.

In certain embodiments, a device or method can be useful to hold two pieces of anatomical soft tissue or organ together; the tissue may be lumenal (e.g., a urethra), muscle, tendon ligament, etc.; the two pieces of tissue may be of the same type or of two different types; for example muscle may be connected to muscle, or muscle may be connected to a tendon or ligament. Alternate embodiments of methods and devices can be used to connect another item such as a surgical implant, to soft tissue or an organ.

Methods and devices may be for general surgery at any location of a patient's body, and also for certain types of surgery specific to body regions. Methods and devices may be useful for securing items in a pelvic region, for cardiac surgery, and for plastic surgery procedures in any area of the body such as a face, legs, abdomen, stomach, for connecting items that include related muscle, fascia, and skin.

The description shows tissue fasteners, tissue anchors, or "sutureless" tissue fasteners (any of which may be referred to herein as a "soft tissue anchor") that can be useful to secure to a soft anatomical tissue (e.g., a tissue or organ), to either secure an implant material to the soft tissue or organ, or to secure another soft anatomical tissue or organ to the first soft anatomical tissue or organ.

The soft tissue anchor can generally include two ends (a lead end and a follow end), connected by a tie. The lead end and the follow end can be of any of various configurations that allow placement of the soft tissue anchor at soft tissue, and prevent removal of the soft tissue anchor from the soft tissue after placement.

A soft tissue anchor delivery device (or "insertion tool") can be useful to engage the soft tissue anchor and place the anchor at soft tissue. The delivery device can be capable of transvaginal use, laparoscopic use, or use through an open incision (e.g., open abdominal incision) to place the soft tissue anchor and optionally a surgical implant at a desired surgical site. Examples of soft tissue anchors include an aperture at the lead end. An exemplary soft tissue anchor delivery device (an "insertion tool") can include a distal end that engages the lead end (e.g., at the aperture) to allow the delivery device to push the lead end of the anchor through tissue.

Certain exemplary soft tissue anchors can include a lead end in the form of an elongate leg, and a follow end in the form of an elongate leg, each having an aspect ratio (length divided by a width or other cross-sectional dimension) of at least 7. A tie, also having an aspect ratio of at least 7, can connect the lead end leg to the follow end leg. Other exemplary soft tissue anchors can include a lead end that includes a tapered length-wise profile, and a follow end that includes either a leg or a connector that connects to the lead end.

As one application of the usefulness of the described tissue anchors, certain devices, systems, and methods as described can be used to treat pelvic conditions such as incontinence (various forms such as fecal incontinence, stress urinary incontinence, urge incontinence, mixed incontinence, etc.), hernia, vaginal prolapse (including various forms such as enterocele, cystocele, rectocele, apical or vault prolapse, uterine descent, etc.), levator muscle conditions (e.g., avulsion) and other conditions caused by muscle and ligament weakness, hysterectomies and the like. As explained, the soft tissue anchors, methods, and devices described herein are also understood to be useful for other general surgical procedures, non-surgical medical procedures, and specialty surgical procedures such as plastic surgery.

In one aspect, the invention relates to a soft tissue anchor. The soft tissue anchor (a.k.a., fastener or tissue fastener) includes a lead end having an aperture, a follow end, and an elongate flexible tie having a first tie end and a second tie end. The first tie end is connected to the lead end and the second tie end is connected to the follow end.

In another aspect the invention relates to a combination of a soft tissue anchor and an insertion tool. The soft tissue anchor includes a lead end having an aperture, a follow end, and an elongate flexible tie having a first tie end and a second tie end. The first tie end is connected to the lead end and the second tie end is connected to the follow end. The insertion tool includes a distal end having a needle and a needle tip adapted to engage the aperture to allow the insertion tool to push the lead end through tissue.

In another aspect the invention relates to a method of connecting an implant to tissue or an organ. The method includes providing a soft tissue anchor having a lead end having an aperture, a follow end, and an elongate flexible tie having a first tie end and a second tie end. The first tie end is connected to the lead end and the second tie end is connected to the follow end. The method also includes providing an implant, engaging the implant with the anchor, and placing the anchor at tissue or an organ to connect the implant to the tissue or organ, e.g., to support the implant. An insertion tool having a distal end having a needle and a needle tip adapted to engage the aperture to allow the insertion tool to push the lead end through the tissue or organ, may optionally be used to place the soft tissue anchor at the soft tissue (e.g., organ).

In another aspect the invention relates to a method of connecting tissue (e.g., anatomical tissue such as soft tissue or tissue of an organ, etc.). The method includes providing a soft tissue anchor having a lead end having an aperture, a follow end, and an elongate flexible tie having a first tie end and a second tie end. The first tie end is connected to the lead end and the second tie end is connected to the follow end. The method includes accessing a first anatomical tissue or organ, accessing a second anatomical tissue or organ, engaging the first anatomical tissue or organ with the anchor, and engaging the second anatomical tissue or organ with the anchor to connect the first anatomical tissue or organ with the second anatomical tissue or organ.

BRIEF DESCRIPTION OF THE DRAWINGS

FIGS. 1C and 1D show a top and a side view of a soft tissue anchor.

Figures 1A, 1B:
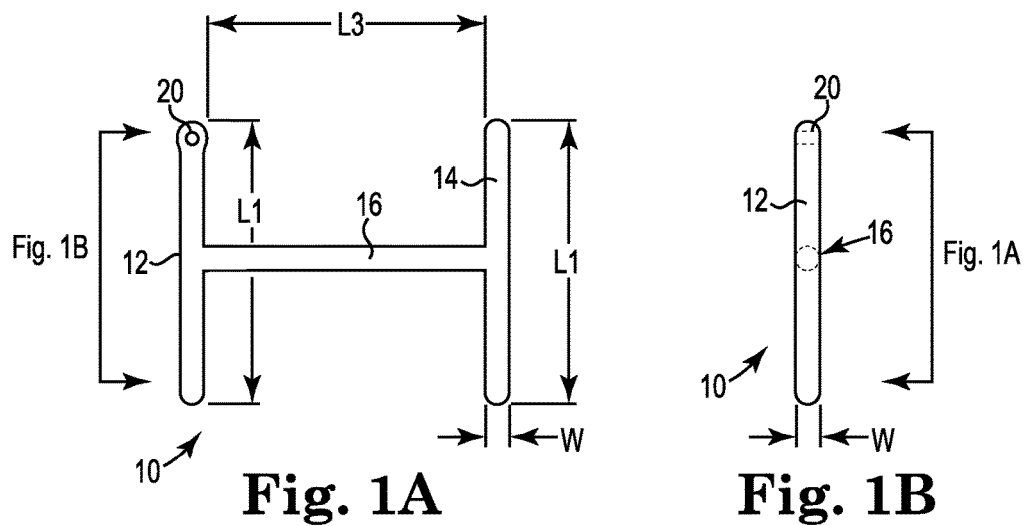
FIGS. 1A and 1B show a top and a side view of a soft tissue anchor.

All figures are schematic and are not to scale.

DETAILED DESCRIPTION

This description relates to the use of tissue fasteners, tissue anchors, or "sutureless" fasteners useful to secure to an anatomical tissue, to either secure an item such as an implant material to the tissue or to secure another anatomical tissue to the first anatomical tissue. Much of the present description relates to methods of using a tissue fastener in certain surgical applications, such as to secure an implant to a pelvic tissue for treating, e.g., hernia, incontinence, prolapse, or the like. This emphasis in the present description of those exemplary applications, of a tissue fastener being used at a pelvic tissue, is not to be considered as limiting the broader concepts and principles found in the present descriptions. In specific, various and multiple other medical and surgical medical uses of the described tissue fasteners, insertion tools, systems, and methods will be apparent based on the present description, and can include any past, present, or future use or application by which as soft tissue anchor or suture can be secured to anatomical tissue.

Pelvic floor disorders include hernia, cystocele, rectocele, enterocele, incontinence (e.g., urinary and fecal incontinence), and uterine and vaginal vault prolapse, among others. These disorders typically result from weakness or damage to normal pelvic muscle or support systems. Common etiologies include childbearing, removal of the uterus, connective tissue defects, prolonged heavy physical labor, and postmenopausal atrophy.

Vaginal vault prolapse is often associated with a rectocele, cystocele, or enterocele. It is known to repair vaginal vault prolapse by connecting vaginal tissue to supraspinous ligament by sutures, or to attach vaginal tissue through mesh or fascia to tissue at a region of the sacrum. Many patients suffering from vaginal vault prolapse also require a surgical procedure to correct stress urinary incontinence that is either symptomatic or latent.

A sacral colpopexy (SCP) is a procedure for providing vaginal vault suspension. It may be performed through an abdominal incision ("open surgery"), a vaginal incision, or laparoscopically, and entails suspension (by use of an implant such as a strip of mesh) of the vaginal cuff to a region of sacral anatomy such as the sacrum (bone itself), a nearby sacrospinous ligament, uterosacral ligament, or anterior longitudinal ligament at the sacral promontory. In some SCP procedures that also involve a hysterectomy, an implant can attach to posterior vaginal tissue remaining after removal of the uterus and cervix, and attaches also to anatomy to support the vaginal tissue, at or around the sacrum such as to uterosacral ligaments or to the sacrum itself (i.e., to a component of the sacral anatomy).

Devices, systems, and methods as described herein can be useful for placing a pelvic implant in a sacral colpopexy procedure, but can also be useful in treating other pelvic conditions, such as a hernia, urinary or fecal incontinence in a male or female patient, or defects, injury, or prolapse of levator tissue. Sling procedures for treating urinary incontinence include surgical methods that place a supportive implant such as a sling to stabilize or support the bladder neck or urethra. A variety of different supportive implants and sling procedures are known. Slings and methods can differ based on the type of sling material and anchoring methods used, and placement and technique for placing and supporting the sling, including tissue to be supported. In some cases, a sling is placed under the bladder neck and secured via suspension sutures to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures are disclosed in U.S. Pat. Nos. 5,112,344; 5,611,515; 5,842,478; 5,860,425; 5,899,909; 6,039,686; 6,042,534 and 6,110,101.

As used herein, the terms "anchor" and "fastener" refer non-specifically to any structure that can connect tissue, or that can connect an implant to tissue, e.g., of a pelvic region. The tissue may be soft tissue such as a muscle, fascia, ligament, tendon, or the like (e.g., supportive tissue), or tissue of a prolapsed organ such as vaginal tissue ("supported tissue"), among others. The anchor or fastener may be any known or future-developed structure useful to connect to such tissue, including but not limited to an "H"-style or "T"-style plastic soft tissue anchors as shown herein, such as at FIGS. 1A, 1B, 1C, and others.

Examples of systems, devices, tools, implants, etc., described herein are directed to medical or surgical instruments, assemblies, implantable supportive implants, systems, and related methods for treating a pelvic condition including prolapse (e.g., any form of vaginal prolapse), urinary incontinence, fecal incontinence, levator defects, etc., in a male or female patient, and hernias, or for general surgical procedures or other specialties such as plastic surgery. In pelvic treatment applications, an implant can be implanted in a male or a female to treat a condition such as prolapse, urge incontinence, mixed incontinence, overflow incontinence, functional incontinence, hernia, and the like.

An implant for placement to treat a pelvic condition can include a tissue support portion (or "support portion") that can be used to support a urethra (including a bladder neck), bladder, vaginal tissue (e.g., vaginal apex), levator, rectum, sphincter, abdominal muscle, or other pelvic tissue (referred to herein as "supported tissue"). Supporting a "urethra" refers to supporting tissue that includes the urethra (which can refer to the bladder neck), and that can optionally include tissue adjacent to a urethra such as bulbospongiosus muscle, corpus spongiosum, or both.

An implant can additionally include one or more extension portion (otherwise known as an "end" portion or "arm") attached or attachable to the tissue support portion. Normally, for treating incontinence or for treating vaginal vault prolapse, an implant can include two or four extension portions. Extension portions are elongate pieces of material (e.g., mesh, molded implant material, suture, or biologic material) that extend from the tissue support portion and either are or can be connected to the tissue support portion, and are useful to attach to anatomical features or "supportive tissue" in the pelvic region (e.g., using an anchor or fastener) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's co-pending application having U.S. Publication No. 2010/256442, filed Aug. 8, 2008, by Ogdahl, entitled SURGICAL ARTICLES AND METHODS FOR TREATING PELVIC CONDITIONS, the entirety of which is incorporated herein by reference). Also see U.S. Publication No. 2011/0034759 and International Patent Publication Nos. WO 2010/093421, WO 2011/063412, and WO 2011/072148, the entireties of which are incorporated hereby by reference. Soft tissue anchors, systems, and method as described herein can be useful with any of these and similar surgical implants and methods, e.g., by which a soft tissue anchor as described is used to secure an extension portion of an implant at a location to secure the implant to tissue, e.g., at supportive tissue; the soft tissue anchors can alternately or additionally be used in such methods for securing a portion of an implant (e.g., central portion or support portion) to tissue that is supported by the implant, such as vaginal tissue, bladder, tissue, muscle tissue (e.g., levator muscle tissue) or another tissue or organ being supported by the implant.

In exemplary uses, each extension portion can extend from the location of attachment with the tissue support portion, through pelvic tissue or space, and optionally be attached to supportive tissue within the pelvic region. For certain procedures, the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. Other supportive tissue for different procedures (e.g., prolapse) may be a ligament, tendon, or muscle in the pelvic region such as an arcus tendineus, sacrospinous ligament, uterosacral ligament, abdominal muscle (e.g., for hernia repair), or levator muscle, or tissue of a region of a sacrum such as an anterior longitudinal ligament.

An implant may include portions, pieces, or sections that are synthetic or of biologic material (e.g., porcine, cadaveric, etc.). Extension portions may be, e.g., a synthetic mesh such as a polypropylene mesh, a suture, a biodegradable suture, a molded implant material, or the like. The tissue support portion may be synthetic (e.g., a polypropylene mesh or a molded material) or biologic. Examples of implant products that may be useful according to the present description, optionally with modification in a manner as described herein, include implant products sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, MiniArc®, InVance™, and AdVance™ for treating urinary incontinence.

Pelvic implant installation procedures (e.g., SCP procedures) may be performed through an abdominal opening (by open abdominal surgery), laparoscopically (e.g., through a laparoscopic incision in an abdomen), transvaginally in a female patient, or through a medial (perineal) incision in a male patient. According to methods described herein, a soft tissue anchor delivery device can be used to deliver a soft tissue anchor to a surgical site of a pelvic implant installation procedure, to secure an implant material (e.g., an extension portion of an implant) at the surgical site. A soft tissue anchor delivery device can be used in the described methods in a minimally invasive transvaginal SCP procedure, in a laparoscopic SCP procedure, or in an abdominal SCP procedure that involves an open (non-laparoscopic) abdominal incision. In alternate treatments, a soft tissue anchor delivery device can be used in a transvaginal, laparoscopic, or abdominal procedure for treating other conditions such as female vaginal prolapse (cystocele, enterocele, rectocele), male or female urinary or fecal incontinence, a hernia, or a condition of levator tissue (e.g., prolapsed or damaged levator tissue). Examples of methods and implants useful in pelvic procedures, including sacrocolpopexy procedures, are described in Assignee's co-pending International Patent Application having International Patent Application No. PCT/US2010/062577, filed Dec. 30, 2010, published as WO 2011/082350; Assignee's co-pending provisional patent application having U.S. Ser. No. 61/515,160, filed Aug. 4, 2011; Assignee's co-pending provisional patent application having U.S. Ser. No. 61/515,685, filed Aug. 5, 2011; Assignee's co-pending patent application having U.S. Publication No. 2013/0006061, filed Jun. 29, 2012; Assignee's co-pending application having U.S. Publication No. 2013/0035543, filed Aug. 3, 2012; Assignee's co-pending application having U.S. Publication No. 2013/0035555, filed Oct. 4, 2011; and Assignee's co-pending application having U.S. Publication No. 2012/0022318, filed Oct. 4, 2011, the entireties of which are incorporated by reference.

According to presently described systems, devices, and methods, a soft tissue anchor delivery device can be useful for accessing and delivering a soft tissue anchor to a surgical location in a male or female pelvic anatomy during a transvaginal (in female patients), perineal (in a male), laparoscopic, open surgical, or trans-abdominal pelvic procedure, for example to access tissue of the posterior pelvic region such as to perform an SCP procedure, to perform repair of a hernia, or to treat another pelvic condition. The soft tissue anchor will also attach to an implant material, securing the implant material at a location of the soft tissue anchor and adjacent tissue.

The soft tissue anchor can be prepared from any useful material, for example a useful biocompatible polymer, which may either be bioresorbable or non-bioresorbable. As opposed to a staple, which is typically made of metal or other similar material that is permanently deformed during use, the soft tissue anchor (especially the tie) can preferably be made of a material that is sufficiently flexible and resilient to not become substantially permanently deformed upon being placed using a soft tissue anchor delivery device at a surgical site, through tissue, or upon being otherwise manipulated or handled during uses described herein. Examples of useful materials include flexible plastics such as polyethylene, polypropylene, and other thermoplastic or thermoformable materials, as well other types of biocompatible and optionally bioabsorbable or bioresorbable materials. Exemplary bioabsorbable materials include, e.g., polyglycolic acid (PGA), polylactide (PLA), copolymers of PGA and PLA.

The soft tissue anchor can be of a type sometimes referred to herein as a sutureless anchor or a plastic fastener, which is different from items commonly referred to as a suture, a knot, or a staple; soft tissue anchors of the type described herein are sometimes referred to as sutureless anchors or plastic fasteners that can be plastic anchors that include two ends (e.g., two legs) and a tie. A first end (referred to as a "lead end") includes an aperture, and may be elongate or otherwise shaped and dimensioned (with sufficient cross-section and mechanical properties) to function as described herein. A second end (referred to as a "follow end") may be elongate or otherwise shaped and dimensioned (with sufficient cross-section and mechanical properties) to function as described herein. The lead end and the follow end are connected by the elongate flexible tie; a first end of the elongate flexible tie connects to the lead end, and a second end of the tie connects to the follow end. Exemplary anchors can be in the form of an "H" or "I." Other are also useful, such as a form wherein the tie is bent or curved.

The soft tissue anchor and its constituent lead end, tie, and follow end, can be of any useful dimensions. In use, the lead end, the follow end, and the tie work together to engage tissue and tissue, or tissue and an implant, to secure the tissue and tissue or tissue and implant at a therapeutic or otherwise desired surgical configuration.

Figure 2A:
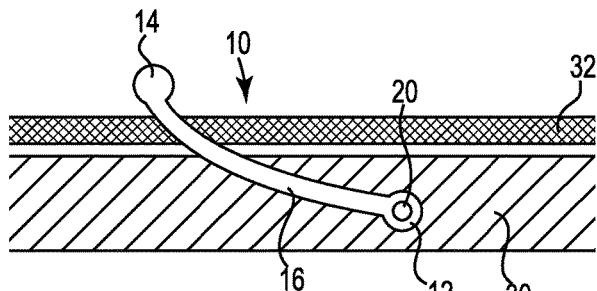
FIGS. 2A, 2B, 2C, 2D, and 2E show use configurations of exemplary soft tissue anchors, wherein the soft tissue anchor engages soft tissue and an implant material.

In one exemplary use configuration, as shown at FIG. 2A, lead end 12 is placed below tissue 30. Tie 16 extends from lead end 12, through a path within tissue 30, along a length external to tissue 30 and through implant 32. Follow end 14 remains external to tissue 30 and on a proximal side of implant 32. (The term "proximal side" in this context refers to a position on a side of the implant away from tissue; a "distal" side is a side of the implant located relatively closer to the tissue.) Implant 32 is held in place against tissue 30 by follow end 14. Alternately, the illustrated implant may be tissue (e.g., soft tissue, tissue of an organ, skin, muscle, etc.), in which case the method connects one tissue to another tissue (e.g., organ).

Figure 2B:
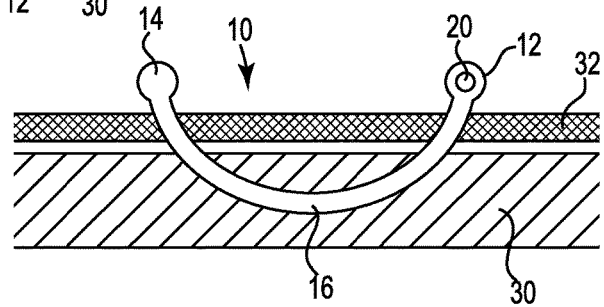

In another exemplary use configuration, as shown at FIG. 2B, lead end 12 is passed into and through a complete path out of tissue 30 to place the tie 16 within a tissue path below or within the tissue 30; lead end 12 exits tissue 30 and (optionally) engages implant 32; follow end 14 remains external to tissue 30 and on a proximal side of implant 32. Tie 16, placed below or within tissue 30, extends between lead end 12 and follow end 14, passing through the tissue path; lead end 12 and follow end 14 remain external to tissue 30 and one or optionally both of lead end 12 and follow end 14 engage (e.g., pass through) implant 32 such that tie 16 engages tissue 30 and lead end 12, follow end 14, or both, are located on a proximal side of implant 32 to hold implant 32 against tissue 30.

An optional feature of the embodiment at FIG. 2B allows for follow end 14 to be folded over, external to tissue 30 and on a proximal side of implant 32. See FIGS. 2C and 2D. Follow end 14 includes handle 22 and one or more connector in the form of aperture 18 that is dimensioned (and sufficiently flexible) to allow aperture 18 to be placed over lead end 12 to secure follow end 14 to lead end 12. Handle 22 is optional, and can be useful to facilitate manipulation of follow end 14 during a surgical procedure. Follow end 14, remaining external to tissue 30 and on a proximal side of implant material 32 can be placed to engage lead end 12 (also external to the tissue) to form a loop that extends around implant 32 (on a proximal side of implant 32) and through tissue 30 (on a distal side of implant 32). Alternately, the implant may be tissue (e.g., soft tissue, tissue of an organ, skin, muscle, etc.), in which case the method connects one tissue to another tissue (e.g., organ). (Note that in FIGS. 2C and 2D, the implant (which may alternately be anatomical tissue) is attached as illustrated by a surface of the implant being placed against a surface of the tissue; alternately, an end of an implant (alternately tissue) can be placed against or abutted against an end of the tissue for an end-to-end-type connection.)

Figure 2C:
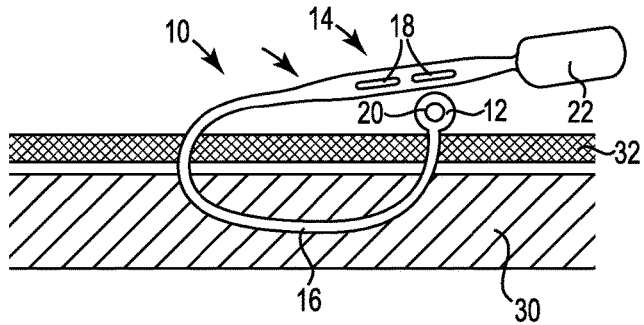
Figure 2D:
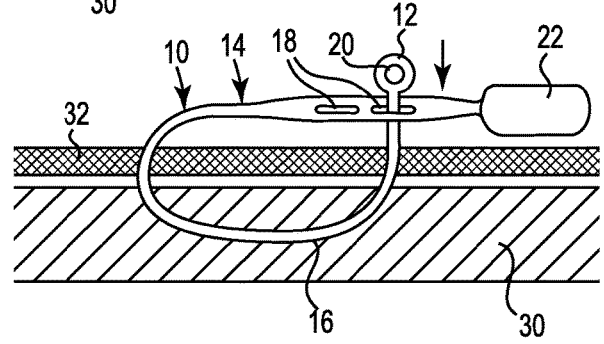
Figure 2E:
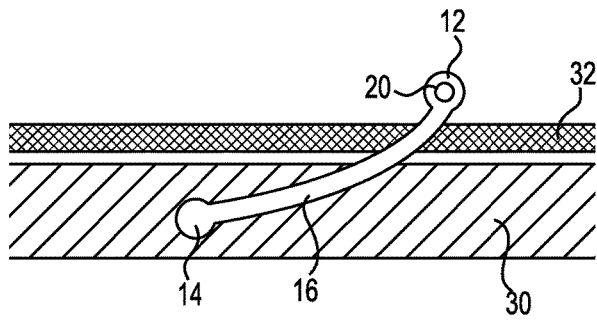

In another exemplary use configuration as shown at FIG. 2E, lead end 12 can be passed through tissue 30 and in engagement with implant material 32 (e.g., through an aperture); follow end 14 is placed below tissue 30 and implant 32 is held against tissue 30 by lead end 12. Alternately, implant 32 may be tissue (e.g., soft tissue, tissue of an organ, skin, muscle, etc.), in which case the method connects one tissue to another tissue (e.g., organ).

The soft tissue anchor and its constituent lead end, follow end, tie, and aperture, etc., can be of any dimensions useful to allow use of the soft tissue anchor according to a medical use or a surgical use to connect tissue to tissue or to connect tissue to an implant, such as by a transvaginal, laparoscopic, or open surgical method. The overall size and mechanical properties (e.g., flexibility) of the soft tissue anchor can be such that the soft tissue anchor can be inserted through a transvaginal, laparoscopic, or open surgical opening or incision. For a laparoscopic incision, the soft tissue anchor must be sufficiently small and optionally flexible to allow insertion through a laparoscopic cannula and a small laparoscopic incision, as are used in laparoscopic techniques. Preferred soft tissue anchors may be flexible, to allow improved ease of placement through a surgical incision or laparoscopic cannula. Specific dimensions of the lead end, the follow end, and the tie, may also be as required to function in the manner described herein, e.g., to secure a surgical implant to tissue.

A lead end can functionally have dimensions (e.g., a cross-sectional profile), shape, form, and mechanical properties that in combination are sufficient to allow the lead end to be passed into or through soft tissue, and such that the lead end once passed into or through the tissue resists movement in a reverse direction and does not become removed from the tissue after placement. The lead end can have a lead end cross-sectional profile (when viewed along a longitudinal axis of the tie at a connection with the lead end) and mechanical properties (e.g., general flexibility but sufficient rigidity) to inhibit or prevent movement of the lead end through tissue in a direction opposite its direction of placement in the tissue, i.e., toward the follow end, after the lead end has been placed through or within the tissue (see FIGS. 2A through 2E). In preferred fasteners, the combined cross-sectional profile (area, dimensions, or both) and mechanical properties of a lead end will prevent removal of the tissue fastener from soft tissue after placement. A cross-sectional profile of the lead end (when viewed along a longitudinal axis of the tie at a connection with the lead end) can include an area (a cross-sectional area), or at least one cross-sectional dimension, that is greater than the area or largest cross-sectional dimension of the tie. Alternately or additionally, a lead end can have dimensions (e.g., a cross-sectional profile) and flexibility sufficient to pass through an implant material (e.g., at an aperture) and thereafter retain the implant material at a location along the length of the tie adjacent to the lead end, to keep the implant material located on the tie and adjacent to and external to tissue if the lead end is passed through tissue and then through implant material (see FIG. 2B) external to tissue.

A lead end includes an aperture adapted to engage a tip at a distal end of a soft tissue anchor delivery device to allow the tip to push the lead end into soft tissue (which includes any type of anatomical soft tissue, including organs), optionally through a tissue path traversing (entering, passing through, and exiting) a segment of the soft tissue. The aperture can be of a useful dimension and can be located at a useful location of the lead end at any orientation relative to the lead end or other component of the tissue fastener, such as the tie. The aperture may be circular, cylindrical, notched, or otherwise shaped in a manner that corresponds to a tip of an insertion tool, e.g., to require a specific orientation between the tip and the aperture (and tissue fastener) during use. The size of the aperture can be useful to engage the tip, and can be of a scale suitable for the anchor. To provide an idea of the scale for certain anchors useful in surgical application such as to treat a pelvic condition, a useful range of diameter or other cross-sectional dimension for the aperture may be, e.g., from about 0.005 inch to about 0.05 inch, e.g., from about 0.01 to about 0.03 inch.

An example of a lead end can be type of lead end that is formed in a shape of a straight (or curved) elongate leg having a length that is angled relative to (e.g., transverse to) a length or longitudinal axis of the tie at the connection between the tie and the lead end (see FIG. 1A), and that is connected to the tie at a location between ends of the elongate leg, such as a medial location. See FIGS. 1A, 1B, 1C, and 1D. An elongate "leg" is a type of lead end or follow end that has a length that is substantially greater than cross-sectional dimensions (e.g., width); a "leg"-type lead end or follow end may have an aspect ratio (length divided by width) of at least 7, e.g., at least 10.

An aperture may be located at one end of a lead end leg, and may pass through the leg in a direction (measured by a longitudinal axis of the aperture) that is normal to (orthogonal to) a plane of the fastener (defined by the leg and the tie) (see FIGS. 1A and 1B), or may pass through the leg at an angle that is not normal to that plane (see FIGS. 1C and 1D)); a non-normal angle (e.g. an angle in a range from 30 to 60 degrees from normal to the specified plane) may allow a tip of a soft tissue anchor delivery device to engage the aperture at an angle that will improve the ability of the tip to push the soft tissue anchor into tissue.

Another example of a lead end is a type that includes a tapered profile from a leading end of the lead end (which passes first into tissue) to a trailing end of the lead end (which trails when passing into tissue) (a "tapered length profile"), e.g., a profile when viewed from a side, lateral to a longitudinal axis of the lead end, that exhibits a form that may approximate or resemble a dart, an arrow, or another tapered structure that increases in size at a trailing end or portion of the structure relative to the leading end. The tapered lead end of an anchor in general is a structure that is placed at a leading portion of the lead end, or that constitutes the a large portion of or the entire lead end, and that can be pushed into tissue when engaged at a distal end or tip of a delivery device. The tapered lead end may engage the tip of the delivery device at the aperture, which can have an axis that is aligned with an axis of the tip of the delivery device when the tip engages the aperture. The aperture can be formed in a base, e.g., a cylindrical base. Optionally, extending laterally from the base can be one or more lateral extensions, which are tapered from a reduced size at the leading end of the base to a larger size at the trailing end of the base.

A follow end of a tissue fastener can functionally have dimensions (e.g., a cross-sectional profile), shape, form, and mechanical properties that in combination are sufficient to allow an implant or tissue to be located at the tie, adjacent to the follow end, such that the implant or tissue is not able to become removed from the tie by passing over the follow end. The follow end can have a follow end cross-sectional profile (when viewed along a longitudinal axis of the tie at a connection with the lead end), and mechanical properties (e.g., general flexibility with sufficient rigidity, and optional malleability or a contorted shape such as a curve, angle, bend, twist, etc.) to inhibit or prevent the implant or tissue from passing over the follow end. (See, e.g., FIGS. 2A, 2B, and 2E.) Alternatively stated, a follow end may exhibit dimensions, shape, form, and mechanical properties that in combination are sufficient to allow the follow end to be passed into soft tissue such that the follow end, once located within the soft tissue, resists movement and does not become removed from the tissue after placement. See FIG. 2E.

In certain embodiments a follow end can also include a connector adapted to connect the follow end to the lead end, e.g., after placement of the lead end and the tie through or within tissue; the length of the follow end can be sufficiently long to allow the follow end, when located external to tissue and on a proximal side of an implant material or another tissue, to be folded over on the proximal side of the implant or tissue to reach and connect to the lead end, which is also external to the tissue and on a proximal side of an implant or another tissue, with the tie being engaged with the implant and located within the tissue (see, e.g., FIG. 2C).

The connector can be any connector that can be engaged with the lead end during a surgical procedure, and may be any mechanical engagement such as snap-fit engagement, a flexible aperture that can be passed over the lead end, a key-fit, a ratchet mechanism, a zip-tie, etc. In use, after passing the lead end through an implant (alternately tissue) (e.g., and as illustrated, twice) and through tissue such that the tie traverses the tissue, two different portions of the tie pass through two different locations of the implant (alternately tissue), and such that the lead end and the follow end are both on a proximal sides of the implant (alternately tissue) (see FIG. 2C), the connector of the follow end can be reached to and connected to the lead end (optionally while a tip of an insertion tool (not illustrated) is still engaged with aperture 20 of lead end 12); the result is a closed loop formed around the tissue and the implant (alternately another tissue) to secure the implant (alternately tissue) to the tissue. FIG. 2C shows such a follow end being folded over to reach the lead end, which is exposed at a tissue surface and on a proximal side of an implant material (alternately tissue). FIG. 2D shows a connector (e.g., aperture) of the follow end attached to the lead end.

A cross-sectional profile of the follow end (when viewed along a longitudinal axis of the tie at a connection with the follow end) can optionally include an area (a cross-sectional area) or at least one cross-sectional dimension that is greater than the area or the largest cross-sectional dimension of the tie. Alternately or additionally, a follow end can have dimensions (e.g., a cross-sectional profile) sufficient to prevent an implant material from being passed over the follow end; the size, cross-sectional profile, and mechanical properties of the follow end can be sufficient to allow the lead end and the tie to be passed through implant material (alternately tissue) and to engage tissue, with the follow end thereafter being located on a proximal side of the implant material (alternately tissue) to retain the implant material (alternately tissue) at a location along the length of the tie adjacent to the follow end, such as to keep the implant material (alternately tissue) located adjacent to and external to the tissue (see, e.g., FIGS. 2A and 2B). Alternately or additionally, a follow end can have dimensions (e.g., a cross-sectional profile) sufficient to be passed into tissue and be retained at a position in the tissue; the follow end may be placed and retained in the tissue, while the tie and lead end are secured to an implant material held by the tissue anchor adjacent to the tissue. See FIG. 2E.

A tie can be of a sufficient length to allow the tie to secure an implant material to tissue, either with the lead end or the follow end of the soft tissue anchor placed within tissue of a patient (see FIGS. 2A through 2E), or with both the lead end and the follow end located external to the tissue (see FIGS. 2B, 2C, and 2D). A length of a tie can be sufficient to extend the tie between a lead end and a follow end, in any such configuration or any configuration described herein. A tie can have an aspect ratio (length divided by width) of at least 7, e.g., at least 10. A length in a range from about 0.1 to about 1 inch, such as from 0.15 to 0.75 inch, may be useful for certain surgical applications, such as for securing an anchor to pelvic tissue and either another pelvic tissue or an implant material. A tie can be made of a flexible plastic material, and may be either straight or curved. A cross-section of a tie can be of any shape or form, e.g., circular, square, rectangular, oval, angled, or cornered, and may be uniform or varying from end to end; the tie may include varying structure along a length, such as teeth, ridges, or another structure to increase or decrease a frictional property of the tie. A cross-section can have dimensions that are sufficiently small to allow passage of the tie through soft tissue, generally also having cross-sectional dimensions and a cross-sectional profile that are relatively smaller than cross-sectional dimensions and cross-sectional profiles of the lead end and the follow end.

FIG. 1A shows an example of an embodiment of an exemplary soft tissue anchor. Soft tissue anchor 10 includes lead end (or "leg") 12, follow end (leg) 14, and tie 16, all of flexible plastic (e.g., molded). Lead end 12 includes aperture 20 adapted to engage a tip of a soft tissue anchor delivery device to allow the device to push lead end 12 into tissue. Exemplary dimensions of lead end 12 (and follow end 14) can include a length (L1) in a range from about 0.1 to about 1 inch, such as from 0.15 to 0.75 inch. A length of the lead end soft tissue anchor 10 may be the same as or different from the length of the follow end of the same soft tissue anchor. A length (L3) of tie 16 can be in a range from about 0.1 to about 1 inch, such as from 0.15 to 0.75 inch. Each of tie 16, lead end 12, and follow end 14, can exhibit a cross-section that is preferably solid, and that can be of any form, such as a circular, square, rectangular, triangular, oval, or otherwise shaped cross-section. A width dimension (W) of the cross-section (e.g., diameter) of each of lead end 12, follow end 14, and tie 16, can be as desired, with examples of a cross-sectional dimension being from about 0.01 to about 0.1 inch, e.g., from 0.015 to 0.08 inch. FIG. 1B shows a side view of anchor 10; this view shows the cross-sectional profile of lead end (leg) 12 (which is the same as the cross-sectional profile of follow end (leg) 14); the cross-sectional profile has an area equal to length L1 by width (W).

Figures 1B, 1C:
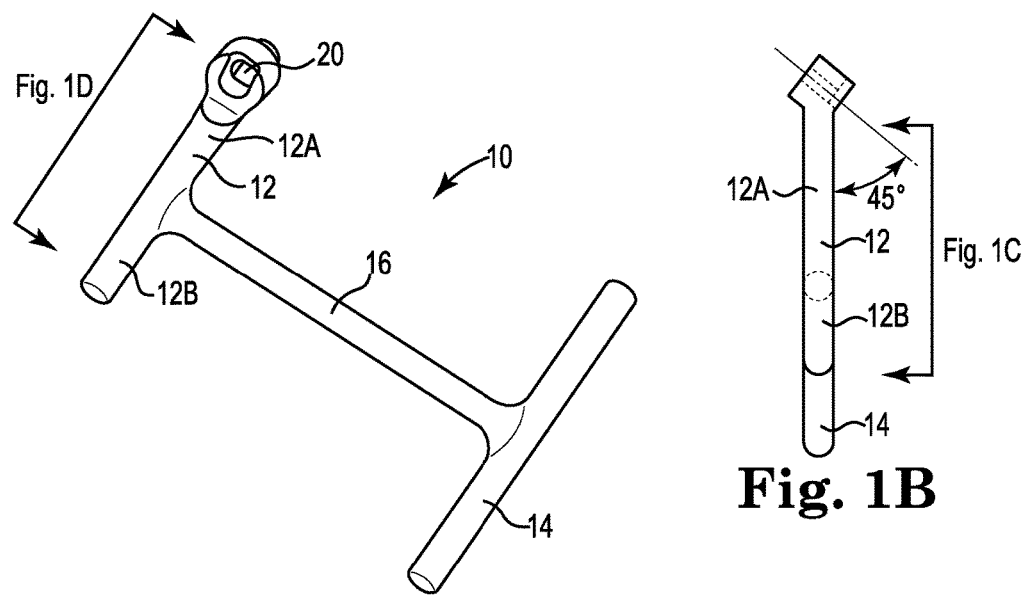

FIGS. 1C and 1D show a variation of anchor 10, also including lead end 12, tie 16, and follow end 14. Lead end 12 of this anchor embodiment is a leg that includes a length that is shorter than a length of follow end 14 (also a leg). Lead end 12 (leg) includes a front segment 12A that extends forward from a connection with tie 16 toward aperture 20 and a back segment 12B that extends backward from connection 16 away from aperture 20. Back segment 12B has a length that is shorter than front segment 12A. A shorter back segment 12B can assist in passing lead end 12 through tissue and out of the tissue at an end of a tissue path to a surface of the tissue; a shorter-length back segment 12B can exit the tissue more easily than if the back segment 12B had a longer length. As another difference, aperture 20 is non-normal to a plane defined by lead end 12 and tie 16, and has a longitudinal axis that is at an angle of about 45 degrees from the longitudinal axis of lead end (leg) 12. See FIGS. 1C and 1D.

Figure 1E:
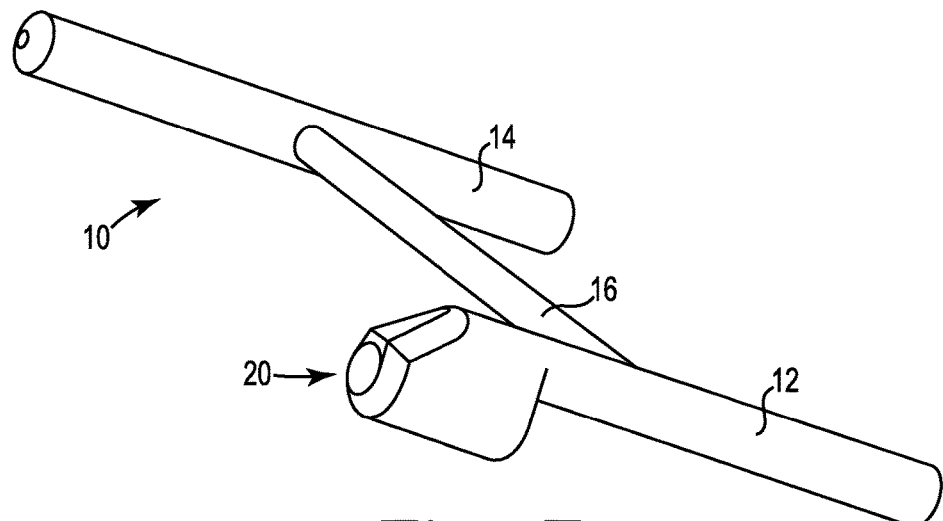
FIGS. 1E and 1F show a top perspective and a bottom perspective view of a soft tissue anchor.
Figure 1F:
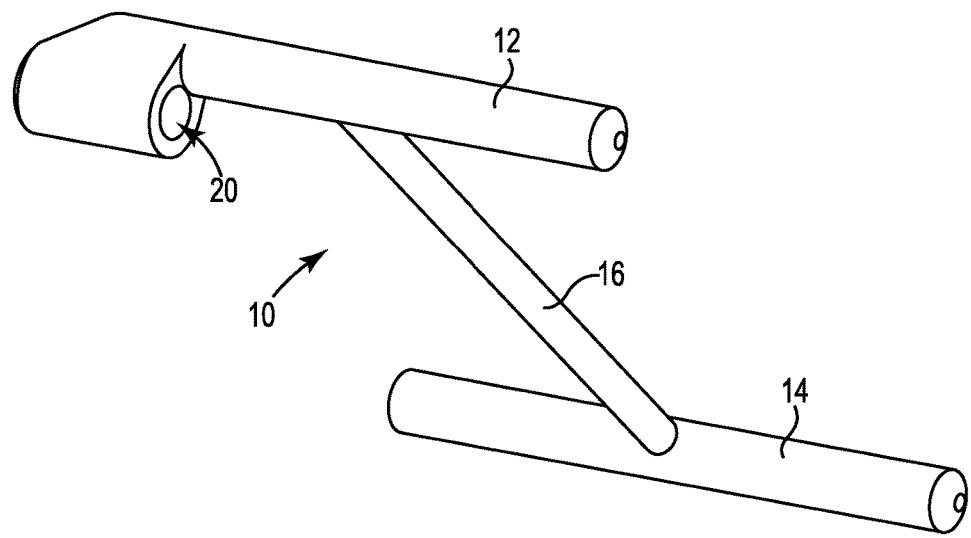

FIGS. 1E and 1F (top perspective and bottom perspective views, respectively) show another variation of anchor 10 of FIG. 1A. In this embodiment, aperture 20 includes a longitudinal axis that is aligned with, i.e., parallel to, but offset from a longitudinal axis of lead end (leg) 12. Other features of this embodiment can be as described for anchors 10 of FIGS. 1A through 1D.

Figure 1G:
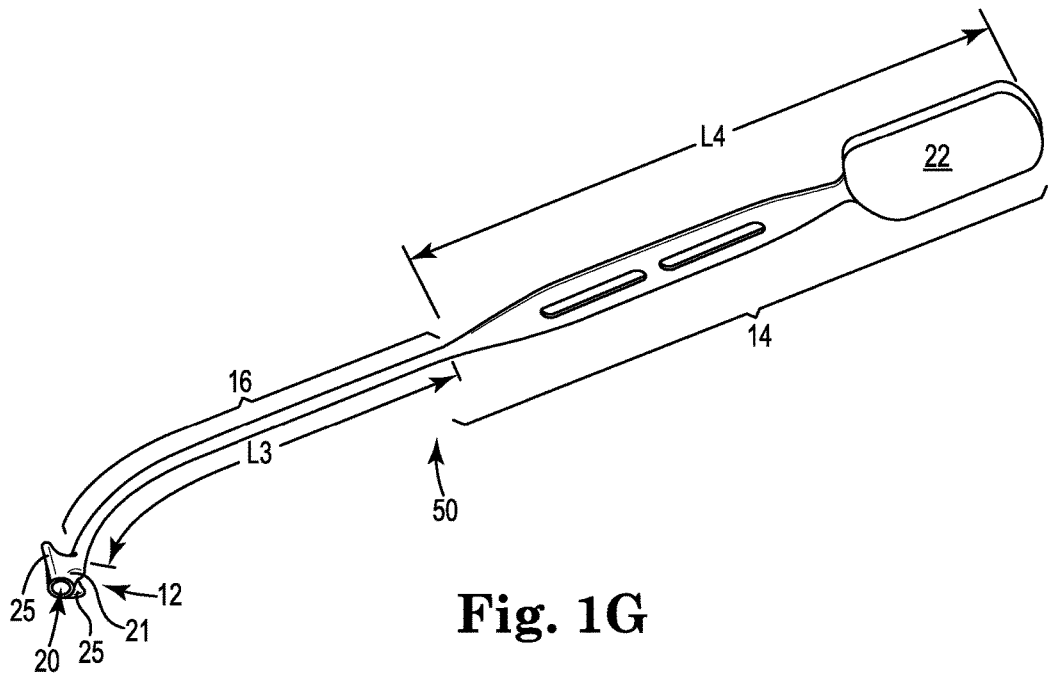
FIG. 1G shows a top perspective view of a soft tissue anchor.
Figure 1H:
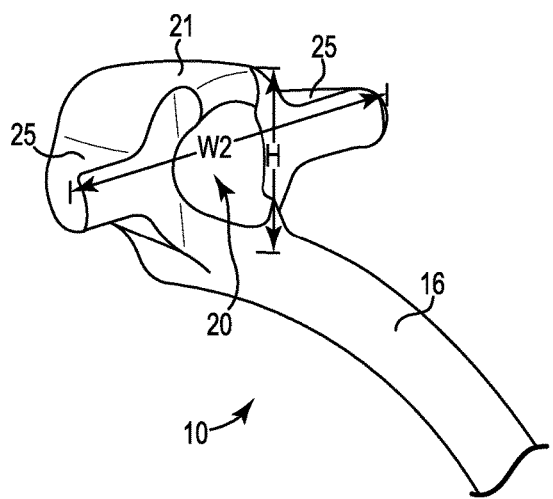
FIG. 1H shows a detailed side perspective view of a lead end of a soft tissue anchor.

Referring now to FIGS. 1G and 1H, illustrated is another embodiment of a soft tissue anchor (10) having lead end 12, follow end 14, tie 16, and handle 22. Tie 16 may be similar to tie 16 of FIGS. 1A through 1F, modified slightly by including a curve (about 90 degrees) at an end of tie 16 that connects to lead end 12; tie 16 can have a length, cross-section, diameter, etc., as described for tissue anchor 10 of FIGS. 1A through 1F, e.g., a length in a range from about 0.3 to about 0.8 inch or from about 0.4 to about 0.7 inch.

Different from anchor 10 of FIGS. 1A through 1F are lead end 12 and follow end 14 of anchor 10 of FIGS. 1G and 1H. Lead end 12 of this embodiment of anchor 10 (shown in more detail at FIG. 1H) includes a tapered length-wise profile. Aperture 20 is defined by cylindrical base 21; aperture 20 includes a longitudinal axis that is at an angle of about 90 degrees relative to a longitudinal axis of tie 16, not including the curved end attached to lead end 12. Extending laterally and in opposite directions away from base 21 are two lateral extensions 25, each having a tapered form, with a reduced size (e.g., distance from the longitudinal axis of aperture 20) at a front end of base 21 (the end that enters tissue first) and an increased size at a back end of base 21. A height (H) of base 21 and a width (W2) of base 21 and lateral extensions 25, at the back end, can be as desired to allow lead end 12 to be passed into tissue (by pushing), and resist movement through tissue in a reverse direction. An example of a useful range for width W2 may be in a range from about 0.35 to 0.8 inch; an example of a useful range for height H may be in a range from about 0.02 to about 0.08 inches, e.g., from about 0.03 to about 0.06 inches.

Follow end 14 includes a length that includes apertures 18 and handle 22. These can be used as shown and described at FIGS. 2C and 2D and related text. Apertures 18 can be formed in follow end 14 in a flexible plastic. Apertures 18 are of a size and flexible form that allow either aperture (as selected during a surgical procedure) to be passed over lead end 12 including base 21 and extensions 25. Once an aperture 18 is placed over lead end 12, the size of lead end 12 relative to the dimensions of aperture 18 should be sufficient to prevent follow end 14 from becoming loose or removed from lead end 12. Handle 22 provides a structure for manipulating follow end 14 during a surgical procedure. A total length (L4) of follow end 14 (including handle 22) can be as desired to allow follow end 14 to function as described herein, to connect to lead end 12 with tie 16 placed in a tissue path and secured to an implant (alternately another tissue) (see FIG. 2D). Length L4 may be, e.g., from about 0.4 to about 0.8 inches, e.g., from about 0.5 to about 0.75 inch. A total length of this embodiment of anchor 10 can be, e.g., from about 0.8 to about 1.4 inch, e.g., from about 0.9 to about 1.2 inch (measured from the end of handle 22 to lead end 12).

A tissue anchor as generally or specifically described herein can be useful to secure tissue to tissue, or an implant material to tissue. Examples of the latter are illustrated at FIGS. 2A through 2E, described previously. The tissue anchor can be placed as illustrated and described, using a soft tissue anchor delivery device (a.k.a. an insertion tool). In use, a tip of an insertion tool is engaged with the lead end, e.g., at an aperture. The insertion tool is used to pass the lead end through tissue and an optional implant material (or another tissue). With the tip of the insertion tool engaged with the aperture, the tip and lead end are passed into tissue, e.g., at a proximal end of tissue path; as the tip and lead end are advanced through tissue, they create a tissue path through the tissue beneath a surface of the tissue; the tissue path extends beneath the tissue surface for a desired distance, and may have a length that is not greater than a length of the tie. The lead end may be passed into the tissue, and the tip of the insertion tool may be withdrawn to leave the lead end within the tissue (see FIG. 2A). Alternately the lead end may be inserted into tissue, passed within the tissue for a desired length and then can be caused to exit the tissue at a distal tissue path opening (see, e.g., FIGS. 2B, 2C, and others). The lead end passes out of the distal tissue path opening; once installed, the lead end is of a physical size and structure, including a cross-section, that is effective to prevent return passage of the lead end back through the distal tissue path opening, or through the tissue path in a manner that would remove the tie from the tissue path. Alternately or additionally, the follow end of the implant may be connected to the lead end to form a loop around an implant and tissue, or tissue and another tissue. See, e.g., FIGS. 2C and 2D. According to different embodiments, a follow end of the fastener may remain external to the tissue path and engage the implant or tissue, or may be placed below tissue (see FIG. 2E).

A soft tissue anchor delivery device (or insertion tool) includes a proximal end with a handle, an elongate shaft for reaching and accessing tissue at a surgical site through a surgical incision, and a distal end. The distal end includes a tip that engages an aperture of the lead end of a soft tissue anchor. With the aperture engaged at the tip, the distal end can be advanced in a forward direction to create a tissue path and push the lead end into or through the tissue. The tie and the follow end will also be advanced behind the lead end.

The shaft of the delivery device can have a length to allow access and delivery of a soft tissue anchor to a desired surgical site when the elongate shaft is placed transabdominally, laparoscopically, or transvaginally, e.g., a length to allow a distal end of the device to reach desired pelvic tissue while the shaft of the device extends through an abdominal, laparoscopic, or vaginal incision, and the proximal end and optional handle are located externally to the patient. A proximal end and optional handle of a soft tissue anchor delivery device may remain external to the patient during use to allow a surgeon or other user to access and manipulate the proximal end, to thereby place and control the distal end at a surgical site.

Exemplary lengths of a shaft of a soft tissue anchor delivery device may be in a range from 10 to 22 centimeters, e.g., from 13 to 20 centimeters, especially for use in a female patient to laparoscopically or transvaginally access a posterior location of a pelvic region such as a region of sacral anatomy. Exemplary diameters of a shaft of a soft tissue anchor delivery device may be suitable to pass through a surgical incision, e.g., laparoscopically through a laparoscopic cannula or a laparoscopic trocar. Exemplary diameters can be in a range from ⅛ inch to 1 inch, e.g., from ⅛ inch to ⅞ inch, or from ⅛ inch to ½ inch.

Figure 3:
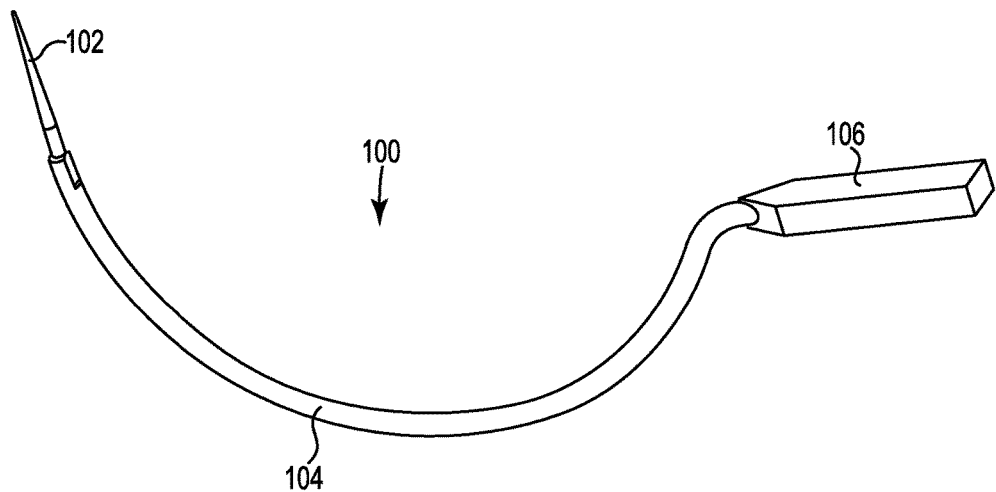
FIG. 3 show an example of a soft tissue anchor delivery device.

FIG. 3 shows an example of a distal end 100 of a soft tissue anchor delivery device (not shown are a shaft and a handle). Distal end 100 includes proximal end 106, curved needle 104, and tip 102. Proximal end 106 may be attached to a shaft extending to a proximal end of a delivery device. Curved needle portion 104 is a rigid curved needle (e.g., of surgical steel or the like) that is shaped for use in forming a tissue path as desired for placing an anchor as described. The illustrated embodiment is curved to a radius of curvature in a range from about 0.1 to 0.6 inch, e.g., from about 0.2 to about 0.5 inch; the curve extends about 180 degrees of arc angle. Curved needle portion 104 as illustrated may be of a material, size, and shape, that are comparable to a curved suture needle. Other embodiments will also be useful for placing a soft tissue anchor as described herein, including needles of different sizes, curvatures (e.g., a straight needle), etc. Tip 102 is of a size (e.g., diameter) useful to engage an aperture of a lead end as described to push the lead end into or through tissue. Desirably, tip 10 can have a sharpened end to facilitate formation of a tissue path.

Figure 4A:
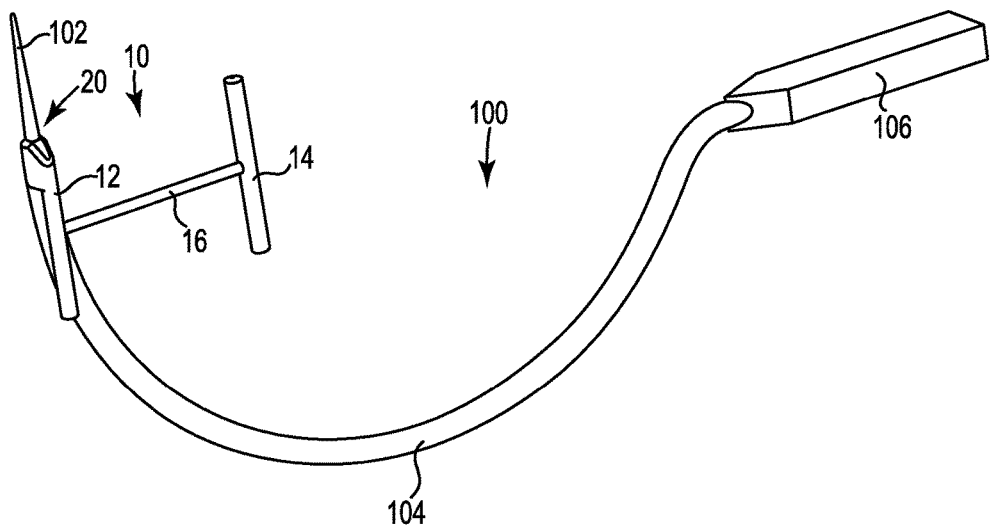
FIGS. 4A and 4B, 5A, 5B, and 6 show examples of soft tissue anchors engaged at a tip of a soft tissue anchor delivery device.
Figure 4B:
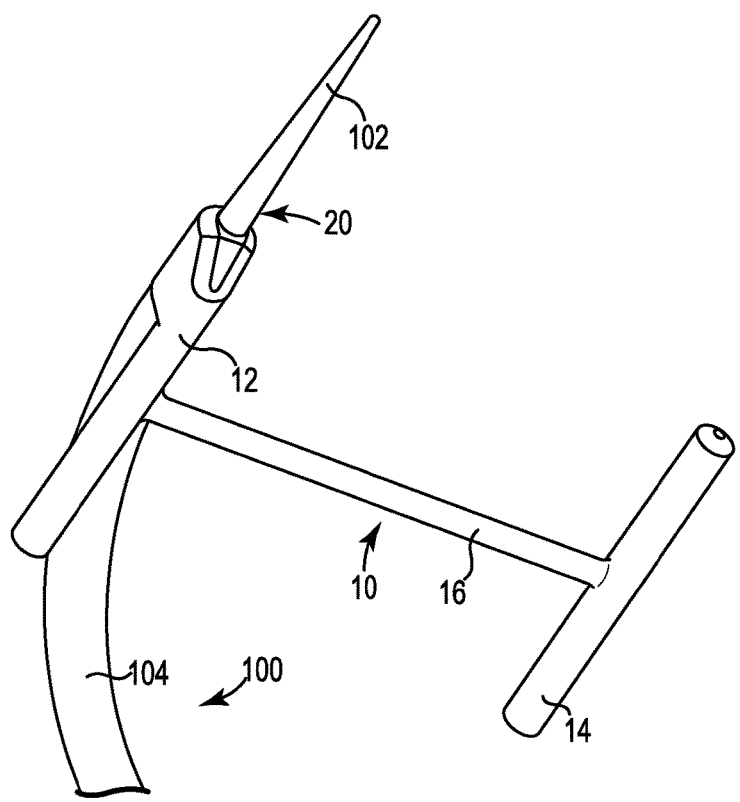

An insertion tool 100 can be useful to place an anchor as described, at tissue, e.g., to secure an implant material or another tissue, to the tissue. FIGS. 4A and 4B show an example of an insertion tool 100 having anchor 10 of FIGS. 1E and 1F, engaged at tip 102. A longitudinal axis of tip 102 is approximately parallel to a longitudinal axis of aperture 20 of anchor 10, and is approximately parallel to a length of lead end (leg) 12. FIG. 4B is a more detailed showing of tip 102 engaged at aperture 20 of anchor 10; as shown, tip 102 passes through aperture 20, allowing for the sharpened end of tip 102 to lead when curved needle portion 104 is advanced into tissue.

Figure 5A:
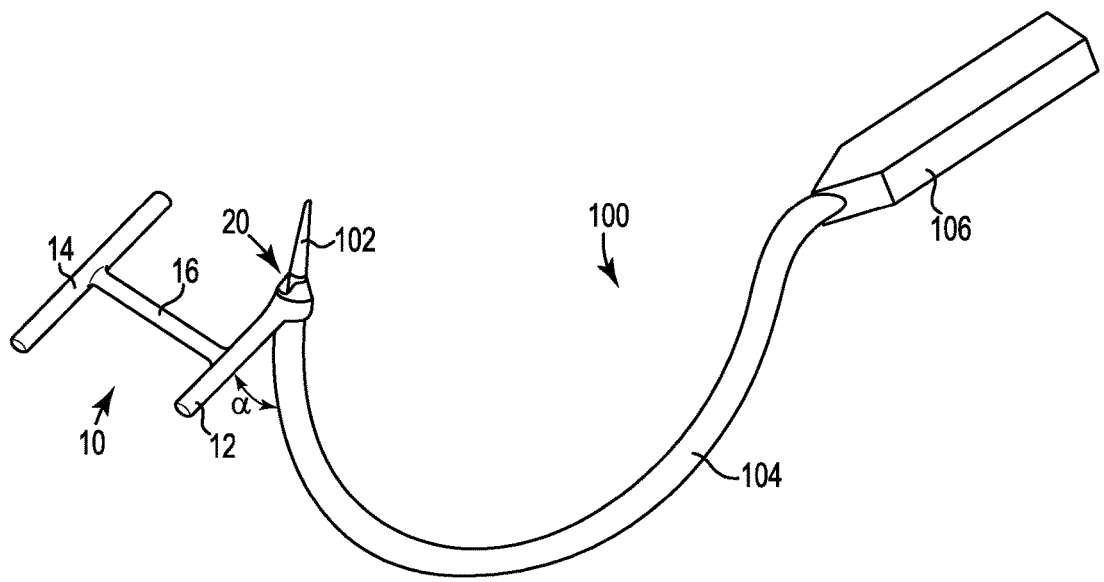
Figure 5B:
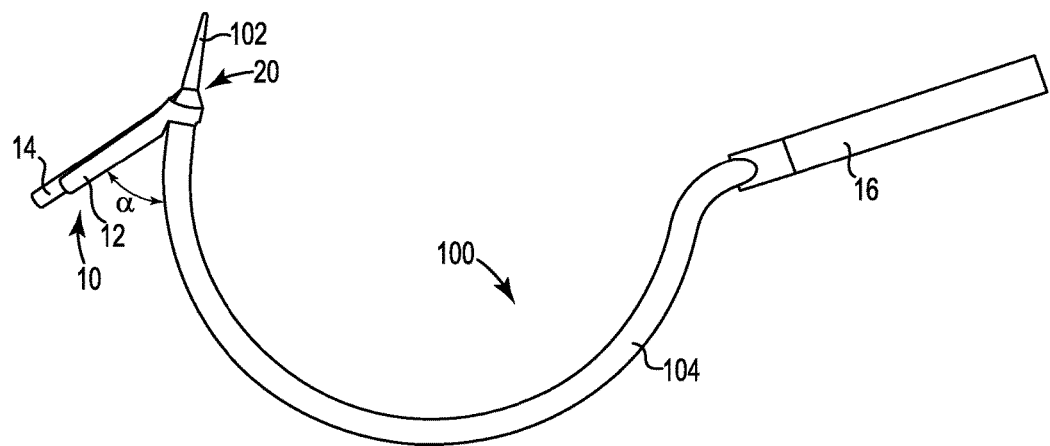

FIGS. 5A (side perspective view) and 5B (side view) illustrate tissue anchor 10 of FIGS. 1C and 1D engaged at tip 102 of insertion tool 100. As illustrated, lead end (leg) 12 is angled about 45 degrees from a longitudinal axis of tip 102, due to the approximately 45 degree angle between a longitudinal axis of aperture 20 and a longitudinal axis of lead end (leg) 12.

Figure 6:
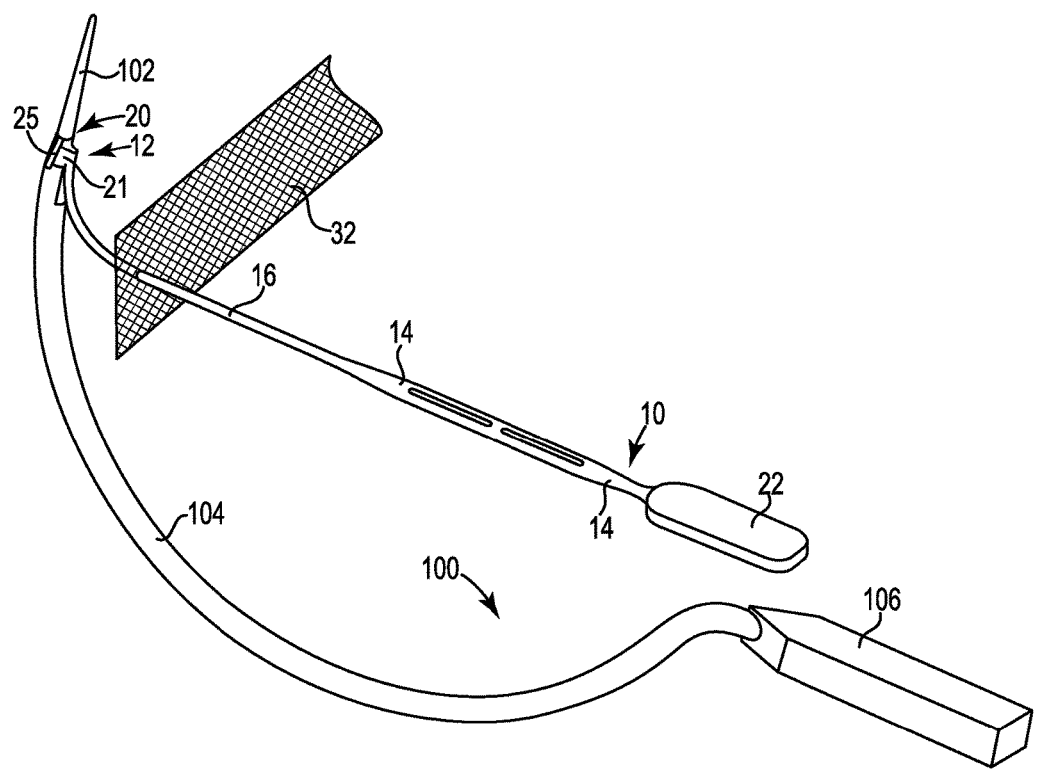

FIG. 6 illustrates (in a side perspective view) tissue anchor 10 of FIGS. 1F and 1G engaged at tip 102 of insertion tool 100. The illustrated combination of insertion tool 100 and anchor 10 can be used as shown at FIGS. 2C and 2D. Anchor 10 includes follow end 14 that includes apertures 18 as connectors for connecting follow end 14 to lead end 12. According to certain exemplary steps, aperture 20 of anchor 10 can be placed onto tip 102; tie 16 is previously or subsequently placed through implant material 32, e.g., through an aperture (as illustrated at FIG. 6, tie 16 is passed through an aperture of implant material 32, but needle 104 is not passed through implant material 32; alternately, needle 104 may be inserted through implant material 32 along with tie 16, e.g., through a single aperture). Tool 100 can be manipulated to pass lead end 12 through tissue 30 to create and traverse a tissue path below the tissue and then exit the tissue; tip 102 and lead end 12 can then be passed through another location of implant material 32 to place lead end 12 on a proximal side of implant material 32 (see FIG. 2C). An aperture 18 of follow end 14 can then be reached to tip 102 (not shown at FIG. 2C or 2D), still engaged with aperture 20, and pulled over tip 102 and led along a length of tip 102 to engage and be pulled over lead end 12 (see FIG. 2D). After follow end 14 is placed over and connected to lead end 12 as shown at FIG. 2D, tip 102 can be removed from aperture 20 of lead end 12 and thereafter removed from implant 32 and tissue 30, leaving implant 10 configured as the loop shown at FIG. 2D.

Soft tissue anchors and delivery devices as described and illustrated can be used and useful by a method of engaging a distal end (tip) of the delivery device with an aperture of the lead end of the soft tissue anchor. The distal end and soft tissue anchor, e.g., when engaged, can be inserted into a surgical incision, for example a transvaginal, laparoscopic, or abdominal incision. The insertion tool can be placed at a desired surgical location, such as a location of soft supportive tissue or at a location of tissue to be supported (e.g., vaginal tissue). For performing an SCP or other procedure, a shaft of the soft tissue anchor delivery device can be passed through an incision to place the distal end and tip of the insertion tool at a region of sacral anatomy or at a region of vaginal tissue. The soft tissue anchor delivery device can be used to secure a portion of a pelvic implant to tissue at the region of sacral anatomy such as to an anterior longitudinal ligament, or to the vaginal tissue. The method can optionally also involve a tool (e.g., retractor or expansion member), implant, adjustable implant, or other device or method, e.g., as described in Assignee's co-pending International Patent Application having International Patent Application No. PCT/US2010/062577, filed Dec. 30, 2010, published as WO 2011/082350, the entirety of which is incorporated by reference.

For other treatment methods, such as hernia repair, plastic surgery, or a general surgical procedure, the distal end of a soft tissue anchor delivery device can be placed at a different anatomical location, depending on the type of repair or treatment.

A soft tissue anchor delivery device as described and its components can be made from any suitable material or combination of materials. Examples include materials that are known to be useful with surgical devices and tools, including stainless steel, nitinol, polycarbonate, polypropylene, polyethylene, fluoropolymer, PET, polyurethane, silicone, polysulphone, and ultem.

Implants, their various components, structures, features, materials and methods may have a number of suitable configurations as shown and described in the previously-incorporated references, or as described herein. Various methods and tools for introducing, deploying, anchoring and manipulating implants to treat prolapse or another pelvic conditions, as disclosed in the previously-incorporated references, are envisioned for use with the present invention as well as those methods and tools identified and described herein.

Also according to embodiments of the methods, implants, tools, and devices described herein, any of the described tissue anchors or insertion tools can be used for placing any desired pelvic implant in a male or a female patient, and for any of a large variety of conditions, such as a pelvic condition; other uses include attaching tissue to tissue or tissue to an implant material in a plastic surgery procedure or a general surgical procedure. The implant can include any structural features useful for such treatment, including any desired size, shape, and optional features such as adjustability and anchoring systems. Any of these features may be previously known, future developed, described herein, or described in documents incorporated herein, for any particular implant and method. For example, the present description relates generally to anchors that can be useful for placing a surgical implant. An implant that is secured by any of the anchors described can be useful to treat a pelvic condition in a male or a female patient; as a single and non-limiting example, an implant that includes or uses an anchor as described can be used in a transvaginal or trans-abdominal SCP procedure to provide support to a vaginal cuff, through an implant that is secured to tissue by the anchor, the anchor being attached at a region of sacral anatomy such as a sacral ligament (e.g., anterior longitudinal ligament, a.k.a. the "anterior ligament" or "longitudinal ligament"), or at tissue of the supported vagina.

The various systems, apparatus, and methods detailed herein are envisioned for use with certain known pelvic implants, repair systems (e.g., for male and female), and method steps, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, and U.S. Patent Publication Nos. 2002/151762, 2010/0174134, 2010/0298630, and 2002/147382. Accordingly, the above-identified disclosures are fully incorporated herein by reference in their entirety.

The presently described systems, their various components, structures, features, materials, and methods may have a number of suitable configurations as shown and described in the previously-incorporated references. Various methods and tools for introducing, deploying, and manipulating device, implants, anchors, and the like as disclosed in the previously-incorporated references are envisioned for use with the present invention as well. Various devices and methods described herein may advantageously facilitate reduction of total procedural time needed to treat a pelvic condition.

All patents, patent applications, and publications cited herein are hereby incorporated by reference in their entirety as if individually incorporated, and include those references incorporated within the identified patents, patent applications and publications.

The invention claimed is:

1. A soft tissue anchor comprising:
   a lead end having an aperture and at least one lateral extension, the aperture configured to receive a needle tip of an insertion tool;
   a follow end including a flexible segment, the flexible segment having at least one slot, the lead end configured to be inserted through the at least one slot; and
   an elongate flexible tie including a first tie end and a second tie end defining a longitudinal axis, the first tie end connected to the lead end and the second tie end connected to the follow end,
   wherein the aperture of the lead end includes a longitudinal axis that is disposed at an angle offset from the longitudinal axis of the tie.

2. The soft tissue anchor of claim 1, wherein the tie has a tie length between the lead end and the follow end, the tie has a first tie cross-section at a location of first tie end connection to the lead end, and the lead end has a lead end cross-sectional profile that is larger than the first tie cross-section.

3. The soft tissue anchor of claim 2, wherein the tie has a second tie cross-section at a location of second tie end connection to the follow end, and the follow end has a follow end cross-sectional profile that is larger than the second tie cross-section.

4. The soft tissue anchor of claim 1, wherein the tie has a length in a range from 0.1 to 1 inch.

5. The soft tissue anchor of claim 1, wherein the aperture has a diameter in a range from about 0.005 inch to about 0.05 inch.

6. The soft tissue anchor of claim 1, wherein the anchor comprises flexible plastic and the anchor does not become permanently deformed when passed through soft tissue.

7. The soft tissue anchor of claim 1, wherein the anchor is configured to be placed through a laparoscopic cannula to be located at a supportive tissue or a supported tissue.

8. The soft tissue anchor of claim 1, wherein the at least one slot includes a first slot and a second slot, the second slot disposed apart from the first slot.

9. The soft tissue anchor of claim 1, wherein the lead end comprises a tapered lengthwise profile, the lead end including a base, the at least one lateral extension including a first lateral extension and a second lateral extension, the first lateral extension extending laterally from the base in a first direction, the second lateral extension extending laterally from the base in a second direction opposite to the first direction.

10. The soft tissue anchor of claim 1, wherein the follow end includes a handle, the flexible segment being disposed between the second tie end and the handle.

11. A method of connecting an implant to tissue or an organ, the method comprising:
   providing the soft tissue anchor as recited at claim 1;
   providing an implant;
   engaging the implant with the soft tissue anchor; and
   placing the soft tissue anchor at the tissue or organ to connect the implant to the tissue or organ.

12. The method of claim 11, wherein the method is for treating a pelvic condition, and the pelvic condition is a condition of a male or female patient selected from the group consisting of: a condition of levator tissue, urinary incontinence, fecal incontinence; hernia, and a prolapse condition.

13. The method of claim 11, wherein the method is a sacral colpopexy comprising laparoscopically placing the soft tissue anchor at a region of a sacral anatomy to hold the implant at the region of sacral anatomy, or laparoscopically placing the soft tissue anchor at vaginal tissue to hold the implant at the vaginal tissue.

14. The soft tissue anchor of claim 1, wherein the aperture is disposed at an orthogonal angle with respect to the longitudinal axis of the tie.

15. A medical device comprising:
a soft tissue anchor including:
   a lead end having an aperture and at least one lateral extension;
   a follow end including a flexible segment, the flexible segment having at least one slot, the lead end configured to be inserted through the at least one slot; and
   an elongate flexible tie including a first tie end and a second tie end defining a longitudinal axis, the first tie end connected to the lead end and the second tie end connected to the follow end,
   wherein the aperture of the lead end includes a longitudinal axis that is disposed at an angle offset from the longitudinal axis of the tie; and
an insertion tool including a distal end, the distal end including a needle and a needle tip configured to engage the aperture to allow the insertion tool to push the lead end through tissue.

16. The medical device of claim 15, wherein the needle is a curved needle having a radius of curvature in a range from about 0.1 to about 0.6 inch.

17. The medical device of claim 15, wherein the needle, with the needle tip engaged with the aperture, is configured to be passed through a laparoscopic trocar.

18. The medical device of claim 15, further comprising:
a pelvic implant.

19. The medical device of claim 15, further comprising:
a pelvic Y-mesh implant configured to treat vaginal vault prolapse.

20. The medical device of claim 15, wherein the aperture is disposed at an orthogonal angle with respect to the longitudinal axis of the tie.

* * * * *